(12) United States Patent
Canham

(10) Patent No.: US 7,332,339 B2
(45) Date of Patent: *Feb. 19, 2008

(54) TRANSFERRING MATERIALS INTO CELLS USING POROUS SILICON

(75) Inventor: Leigh T Canham, Malvern (GB)

(73) Assignee: PSIMedica Limited, Malvern, Worcestershire (GB)

( * ) Notice: Subject to any disclaimer, the term of this patent is extended or adjusted under 35 U.S.C. 154(b) by 265 days.

This patent is subject to a terminal disclaimer.

(21) Appl. No.: 10/854,255

(22) Filed: May 27, 2004

(65) Prior Publication Data

US 2004/0220535 A1 Nov. 4, 2004

Related U.S. Application Data

(62) Division of application No. 09/743,447, filed as application No. PCT/GB99/02383 on Jul. 22, 1999, now Pat. No. 6,770,480.

(30) Foreign Application Priority Data

Jul. 22, 1998 (GB) ................................. 9815819.9

(51) Int. Cl.
*C12N 15/87* (2006.01)

(52) U.S. Cl. .................... 435/459; 435/470; 435/285.3

(58) Field of Classification Search ............. 435/285.1, 435/285.3, 459, 470
See application file for complete search history.

(56) References Cited

U.S. PATENT DOCUMENTS

| 4,784,737 | A | 11/1988 | Ray et al. |
| 5,457,041 | A | 10/1995 | Ginaven et al. |
| 5,484,720 | A | 1/1996 | Wurm et al. |
| 5,635,216 | A | 6/1997 | Thompson |
| 5,858,853 | A | 1/1999 | Shishiguchi et al. |
| 6,033,928 | A | 3/2000 | Eriguchi et al. |
| 6,132,755 | A | 10/2000 | Eicher et al. |
| 6,334,856 | B1 | 1/2002 | Allen et al. |
| 6,503,231 | B1 | 1/2003 | Prausnitz et al. |
| 6,770,480 | B1* | 8/2004 | Canham .................... 435/458 |
| 6,929,950 | B2* | 8/2005 | Canham et al. ............. 435/459 |

FOREIGN PATENT DOCUMENTS

| JP | 06 034361 A | 2/1994 |
| WO | WO91/05519 | 5/1991 |
| WO | WO 92/01802 | 2/1992 |
| WO | WO 96/10630 | 4/1996 |
| WO | WO 97/06101 | 2/1997 |

OTHER PUBLICATIONS

EPO search report of EP 1522578 dated Feb. 16, 2005.*
Beattie K L et al: "Advances in Genosensor Research" Clinical Chemistry, vol. 41, No. 5, (May 1995) pp. 700-706.
Patent Abstracts of Japan vol. 018, No. 250 (p.1736), May 1994 & JP06 034361 (Canon Inc), -Feb. 1994.
Sanford J.C. et al: "Optimizing the Biolistic Process for Different Biological Applications" Methods in Enzymology, vol. 217, 1993, pp. 483-509.

* cited by examiner

*Primary Examiner*—William H. Beisner
(74) *Attorney, Agent, or Firm*—Nixon & Vanderhye P.C.

(57) ABSTRACT

Porous and/or polycrystalline silicon are used in the delivery of substances into cells. The porous and/or polycrystalline silicon can be formed into micropiercers, microneedles and biolistic bullets for penetration of the cell. The control of the pore size and porosity of the porous and/or polycrystalline silicon allows tuning of the bioactivity of the porous silicon. The porous and/or polycrystalline silicon is also resorbable and is therefore resorbed from the cells without leaving any particles or being seen as a foreign body. Methods of manufacturing the porous silicon micropiercers, microneedles, microelectrodes, biolistic bullets, and precipitation of calcium phosphate on a bioactive substrate, and their advantages over known methods of delivering materials into cells.

3 Claims, 4 Drawing Sheets

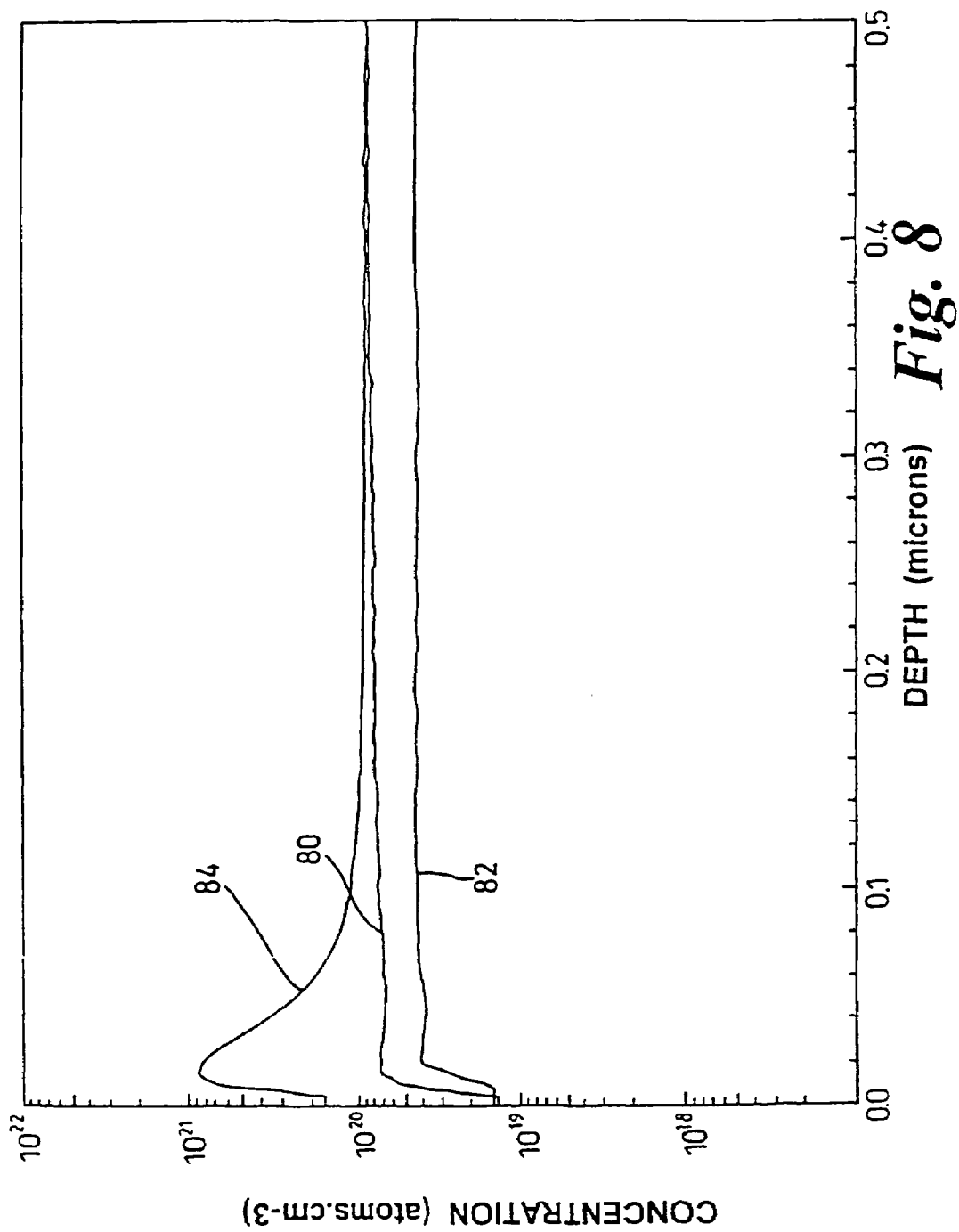

ed into a cell for the purposes of genetic manipu-
TRANSFERRING MATERIALS INTO CELLS USING POROUS SILICON

CROSS REFERENCE TO RELATED APPLICATION

This application is a division of application Ser. No. 09/743,447 filed Jan. 10, 2001 now U.S. Pat. No. 6,770,480, which in turn is a §371 of PCT/GB99/02383 filed Jul. 22, 1999 which claims priority of GB9815819.9 filed Jul. 22, 1998.

This invention relates to ways of transferring materials into cells, and also to a microneedle array.

There are many times when it is necessary to transfer materials into cells, for example nucleic acids or nucleic acid constructs, such as vectors or plasmids, etc. have to be transferrlation. Furthermore, chemicals may also need to be transferred into cells, e.g. nucleotides or stains, and chemicals to affect the physiology of a cell. A number of chemical and mechanical processes have been developed to convey materials into cells. These techniques include:

1. direct microinjection—a needle is inserted into a cell and material expelled through the needle;
2. electroporation the cell membrane is made permeable to some molecules by application of a high voltage shock;
3. biolistics—tungsten or gold particles are coated with the substance desired to be introduced and are shot into the cell;
4. calcium phosphate co-precipitation—cells absorb calcium phosphate, and if DNA/other material co-precipitates with the calcium phosphate it is also taken into the cell:
5. mediated transformation (via liposome, viral, or bacterial vectors): and
6. protoplast transformation.

An aim of one aspect of the present invention is to use a new material to assist in the transfer of substances to cells.

An aim of another aspect of the invention is to provide an improved way of providing small volumes of a substance.

Direct microinjection involves the insertion by a microneedle of DNA directly into the nucleus of individual cells. A glass micropipette linked to a micromanipulator is used to inject $10^{-8}$-$10^{-7}$ µl of material, typically a solution of DNA fragments, into cell nuclei. "Hits" are almost certain, given considerable operator expertise, but the technique is laborious and cannot be applied to a large number of cells.

According to a first aspect the invention comprises a method of transferring a substance into the cell.

Preferably resorbable or bioerodable porous silicon is used.

In one embodiment a microneedle that comprises at least a region of porous silicon is used or an array of such microneedles is used.

According to a second aspect the invention comprises a microneedle (or microneedle array) comprising porous silicon.

According to a third aspect the invention comprises a vehicle for transferring material into a cell, the vehicle comprising, at least in part, porous silicon and material to be transferred into the cell.

Preferably the porous silicon is resorbable. The vehicle may comprise a porous silicon biolistic bullet. The vehicle may comprise a substance which in use will co-precipitate with a co-precipitate substance that is taken into the cell. The vehicle may comprise an electrically-conducting bioactive porous silicon electrode.

According to a fourth aspect the invention comprises the use of porous silicon as a transfer medium for transferring materials into a living cell.

It has been discovered that porous silicon is biocompatible, and it has now been discovered that porous silicon can be corroded in, or resorbed into, a mammalian body without significant detrimental effect. Porous silicon can be used to locate and substantially immobilise biological material (or any substance to be introduced into a cell), with the substance being free enough once in the cell to combine with cell DNA, or otherwise be released to have an effect.

It is known from PCT Patent Application No. WO 96/10630 to have an array of micromachined bulk silicon barbs or tips and to use them mechanically to pierce the plasma membrane of large numbers of cells simultaneously. This is more efficient than piercing a single cell with a single needle, which can result in a laborious operation if hundreds of cells need to have material introduced into them. The tips of WO 96/10630 are, with hindsight, less effective at transferring material (e.g. DNA) into a pierced cell than they might be. It is, for example, proposed in that document to use surface tension forces between closely-spaced tips to hold biological material to be introduced into the cells in the spaces between the tips, and to trap it between the tips (probes) and the substrate.

A proposal is discussed in U.S. Pat. No. 5,262,128 which was published in 1993 and purports to teach the man skilled in the art to make an array of silicon needles using the Liga Processes. It is believed that this document is non-enabling at its filing (and publication) date and is not prejudicial to the novelty of the present invention for that reason. In 1989 when the application was filed, and in 1993 when it was published, the skilled man of ordinary expertise could not make very thin silicon needles having a central lumen as discussed in the document using the techniques discussed. The Liga Process is not suitable for manufacturing hollow needles in silicon and does not enable sloping structures to be made.

U.S. Pat. No. 5,457,041 discloses an array of solid needles made of silicon having ragged tips.

U.S. Pat. No. 5,591,139 discloses a silicon microneedle that is formed in the plane of a silicon wafer.

WO 97/06101 discloses a method for producing bioactive silicon as a wafer, and suggests uses for bioactive silicon in the fabrication of biosensors and in bioassays.

WO 92/01802 discloses the idea of gem substance into a cell by incorporating the substance in a liquid and making the particles of the liquid, and then accelerating the ice particles to penetrate the cells, the ice particles melting after cell-penetration.

JP 06 034 361 discloses a porous silicon atomic force microscope tip. The device does not penetrate the sumacs being imaged.

U.S. Pat. No. 4,969,468 discusses solid metal needles for electrical contact with nerves.

According to another aspect tab invention comprises a cell-penetrating member or micropiercer made of porous silicon.

The cell-penetrating member is adapted to have a substance to be introduced into a cell carried by to porous silicon.

According to another aspect, the invention comprises a cell penetrating member or a micropiercer comprising at least a region of porous silicon. Preferably the substance comprises DNA or RNA, a fragment of DNA or RNA, or a construct of DNA or RNA.

The cell penetrating member or micropiercer is preferably adapted to have a substance to be introduced to a cell carried by porous silicon.

The porous silicon region is adapted to immobilise a substance (e.g. DNA) in comparison with its mobility when provided with a bioinert substance such as titanium. The porous silicon region is preferably at the tip of the cell penetrating member or micropiercer. The cell penetrating member or micropiercer may be a tip or barb, with no central lumen or it may be a needle with a central channel. The cell gene-rating member or micropiercer may have a capilliary or pore network extending from a reservoir or channel to a substance delivery region provided on the surface of the cell penetrating member or micropiercer.

The cell penetrating member or micropiercer may have a coating of porous silicon or it may be porous throughout its cross-section, at least at its tip (or other substance delivery region if that is not the tip). Substantially the whole exterior surface of the cell penetrating member or micropiercer that penetrates a cell in use may comprise porous silicon. The cell penetrating member or micropiercer may be a bulk silicon microtip with a porous silicon coating.

An advantage of holding the substance to be introduced to the cell at the tip of the cell penetrating member or micropiercer itself, instead of in channels/spaces between tips, is that the material is definitely introduced into the cell, and typically deeply into the cell. This may increase the success rate of the operation (in many cases introducing DNA into cells and stable uptake of the DNA/fragment is not statistically very successful—a few percent may succeed, which is why so many cells have to be injected).

Instead of using porous silicon to immobilise the material on the tip/ensure at least some material is present on the tip, other holding means may be used. For example, polycrystalline silicon can hold some substances at grain boundaries. The holding means may comprise a porous material.

It is known to immobilise DNA fragments in macroporous silicon in the field of a flow-through genosensor (Advances in Genosensor Research. K. L. Beattie et al. Clin. Chem. 41, 700 (1995)).

An advantage of porous silicon is that its bioactivity can be tuned by controlling its pore size and porosity. It is therefore possible to create a cell penetrating member or micropiercer with a porous tip with pores tailored to hold/immobilise a particular desired molecule or substance. Of course, the substance will not be so immobilised that at least some of the material cannot leave the tip when the tip is in the cell.

Porous silicon has another great advantage as the choice of material for a cell penetrating member or micropiercer in that micromachining techniques for fabricating small scale devices from silicon exist, e.g. in the electronics industry.

It is known how to make a silicon structure porous (see for example U.S. Pat. No. 5,348,618).

An array of cell penetrating members or micropiercers may be provided. The array is preferably a two-dimensional array of n×m micropiercers. The micropiercers are preferably regularly disposed in a grid pattern, but they perhaps do not need to be.

It is also known to have an array of microtips for a completely different purpose—for field emission cathodes used in vacuum microelectronic applications. Here, a 5 mm square silicon chip will typically contain about 500 microtips of pyramidal shape with tip) widths of 50 mm-1 µm and heights of 10-100 µm, depending upon the manufacturing parameters chosen. With hindsight, these would be suitable for porosification and then use as micropiercers for transferring a substance into cells. It is also even known to haste porous silicon pyramidal cathodes—e.g. Field emission from, pyramidal cathodes covered in porous silicon. P. R. Wilshaw et al. J. Vac. Sci. Techn. B12,1 (1994); Fabrication of Si field emitters by forming porous silicon. D. Kim et al. J. Vac. Sci. Tech. B14, 1906 (1996); and Porous silicon field emission cathode development. J. R. Jessing et al. J. Vac. Sci. Techn. B14, 1899 (1996). However, these are all in a totally different field, and one show a micropiercer having held on it DNA, RNA or any other substance to be introduced into a cell.

According to a third aspect, the invention comprises a method of producing a micropiercer device comprising manufacturing one or more micropiercer projections, and providing substance holding means at or near the tip of the projections.

Preferably the method comprises making at least a part of the projections porous. Preferably the method comprises making the tip of the projections porous or substantially the entire extent of the tips porous, or providing a porous coating on the tip. Preferably the tip is made porous using an HF anodising technique.

According to another aspect, the invention comprises a method of transferring a material into a cell comprising associating the material with a tip portion of a micropiercer and piercing the cell with the micropiercer.

Preferably the method comprises using porous silicon to locate the material at or near the tip portion.

According to a further aspect, the invention comprises a method of genetic manipulation of a cell comprising associating genetic material with a tip portion of a micropiercer, piercing the cell with the micropiercer to allow the genetic material to enter the cell. The genetic material may then be stably incorporated in the cell.

According to another aspect, the invention comprises a microneedle array comprising a plurality of needles extending away from a support, the needles each having fluid transport means adapted to transport fluid from their bases to their tips, and fluid supply means communicating with the fluid transport means and adapted to supply fluid to be injected to the base of the needles.

Preferably the array of microneedles are made of silicon. It may be micromachined, for example from a silicon wafer.

The fluid transport means may comprise a reservoir, which may extend under the needles. The support may have a lower portion, an upper portion, and a channel or reservoir extending between the upper and lower portions, with the needles being provided in the upper portion and the fluid transport means extending to the reservoir or channel.

The fluid transport means may comprise a lumen, or macropore in each needle which may extend generally centrally of the needle through its longitudinal extent. Alternatively, or additionally, the fluid transport means may comprise a pore or capillary network, such as a plurality of mesopores.

The array of needles may be provided on an integrated silicon chip, which may also have a sensor provided on it, the sensor preferably enabling one to monitor in situ the transfection process. For example a photo emitter/detector may be used in association with light emitting markers (e.g. fluorescent) associated with the DNA. It may also be desirable to have a power supply and/or processing circuitry, and/or control circuitry provided on the chip. Arrays of light emitting devises and photodetectors may enable the transfection process to be monitored under high-spatial resolution.

According to another aspect the invention comprises a method of manufacturing a microneedle, or a microneedle array, the method comprising taking a bulk silicon wafer and creating a needle or an array of needles; and creating fluid transfer means extending from the base of the or each needle to its tip.

Preferably, the method comprises providing a network of pores from the base of the or each needle to its tip. The pores may be macropores or mesopores, or for some applications they may even be micropores (but macropores are preferred).

The or each needle may be created using photolithographic techniques such as anisotropic etching and photoresist lithographic techniques.

The silicon substrate may be an n-type substrate with a resistivity in the range of 0.1-10 $\Omega$cm.

The needle or needle array may be planarised, for example by use of a non-conducting mask.

The planarised array may then be treated so as to expose just the tips, for example by using an oxygen plasma treatment and an HF dip to expose the tips alone. The planarised array may also be in filled. The tips can then be anodised to create the pores from the tip to the wafer back surface. The wafer, provided with an array of tips, may then be bonded to another backing member, which may be shaped so as to define a channel or reservoir between the tip-carrying wafer and the backing member.

According to a further aspect the invention comprises a vehicle for transferring material into a cell, the vehicle comprising at least in part resorbable material.

Preferably the vehicle comprises resorbable silicon, such as porous silicon, or polycrystalline silicon. The whole of the vehicle may be made of the resorbable material, or only part of it. The vehicle may comprise bioactive silicon. (By "resorbable" it is meant that the material is corroded/absorbed/eroded/or otherwise disappears when in situ in physiological fluids. By "bioactive" it is meant that the material can induce the deposition of calcium phosphate precipitates on its surface under physiological conditions (when in body fluids)).

If the vehicle is retained in the cell it will be adsorbed/corroded/eroded or resorbed, or partially resorbed, and be less of an irritation/foreign body to the cell in due course.

The resorbable silicon/other material may be used in a biolistics technique. For example the vehicle for transferring material into a cell may be a biolistic bullet.

The vehicle for transferring material into the cell may comprise a biolistic bullet comprising porous silicon.

The bullet may have a substance to be introduced into a cell adhered to it. The bullet may be impregnated with material (e.g. DNA material). It may be substantially saturated with material. The bullet may comprise a submicron silicon particle. The silicon particle may be rendered porous by stain etching techniques. The particle is preferably mesoporous.

A resorbable biolistic bullet would not leave behind in the cell a particle, as do gold or tungsten biolistic bullets. The bullet need not be porous all of the way through—it may have a porous coating. The resorbable bullet need not necessarily be made of porous silicon, or of silicon at all, but porous silicon has been identified as an especially suitable material.

According to another aspect, the invention provides a method of transferring material into a cell comprising the steps of shooting a vehicle carrying said material into the cell.

Preferably the vehicle is the vehicle as hereinabove defined. Preferably the bullet is shot into the cell be means of a pressurised gas, for example helium.

The process of biological biolistics is often used where more standard techniques do not work. Resorbable impregnated materials, such as porous silicon offer biocompatible advantages over corrosion-resistant bulk metal materials.

According to a further aspect the present invention provides a method of making a vehicle for transferring material into a cell comprising the steps of rendering the vehicle at least partially porous and introducing to the vehicle the material to be transferred to the cell.

Preferably the vehicle comprises a silicon bullet, most preferably a submicron silicon particle, which may be rendered porous, preferably mesoporous by stain etching techniques. The bullet may have the material to be introduced to the cell, adhered to it or alternatively it may be impregnated with the material.

The vehicle may be a submicron particle and the material to be transferred to the cell may be co-precipitated (with a precipitate substance) using the vehicle as a nucleation site.

The vehicle for transferring material into a cell may comprise bioactive silicon. The vehicle may have associated with it material to be transferred in a form adapted to co-precipitate with a substance which is taken up by cells. The co-precipitate may be a calcium phosphate precipitate.

According to another aspect the invention comprises a method of introducing material into a cell comprising associating the material with a silicon particle, precipitating calcium phosphate onto the particle to form a calcium phosphate/silicon particle combined particle, and arranging for the cell to uptake the calcium phosphate/silicon particle combination.

In the technique of electroporation the cell membrane can be made permeable by exposing cells to a brief electric shock of very high voltage. Low porosity bioactive silicon is electrically conducting and is suitably developed as an intimate coupling matrix for adherent mammalian cells growing on microelectrode arrays.

By having bioactive silicon, e.g. porous silicon or polycrystalline silicon as one or both electrodes in electroporation apparatus it is envisaged that better DNA transfer takes place.

According to a further aspect the invention comprises a method of electroporation comprising providing an electrically conducting bioactive silicon electrode.

Preferably the method comprises growing cells on the electrode. The method may comprise providing an array of bioactive silicon electrodes, possibly with cells grown on them. The electrode, or electrodes, may be coated with porous silicon or may be of porous silicon throughout their cross-section, at least at a region of their height.

According to a further aspect the invention comprises electroporosis apparatus comprising a bioactive electrode. Preferably the electrode is bioactive silicon, most preferably porous silicon. An array of electrodes, or microelectrodes, may be provided.

The invention may also reside in the use of bioactive silicon, preferably porous silicon, in the preparation of apparatus for the introduction of materials into cells.

It may be helpful to clarify that bioactive materials are a class of materials which when in vivo elicit a specific biological response that results in the formation of a bond between living tissue and that material. Bioactive materials are also referred to as surface reactive biomaterials. Resorbable materials are materials which are designed to disappear or degrade gradually over time in vivo, and they may or may not be replaced with tissue. Bioerodable materials are materials which erode in vivo, with the material possibly being absorbed by cells, or possibly not being absorbed. A bioinert material is a material that elicits no local gross biological response in vivo.

BRIEF DESCRIPTION OF THE DRAWINGS

Several embodiments of the present invention will now be described by means of example only with reference to the Figures, in which:

FIGS. 7 and 8 show SIMS plots demonstrating the affinity of DNA for porous silicon and that it can be released from a porous silicon surface.

FIG. 1 shows a micropiercer 10 in the form of a microtip 12 having a base width A of 50 µm and a height B of 100 µm and a tip width C of 0.5 µm. The surface of the microtip 12 is coated with porous silicon 14 having a depth D of 0.1 µm.

In use, the porous silicon coating 14 immobilises the substance to be delivered to the cell (e.g. DNA/RNA) on the tip itself, which increases the chances of the immobilised substance on the tip being introduced into the living cell.

The pore size and porosity of the porous silicon coating can be controlled to tune the bioactivity of the microtip 12. By controlling the pore size and porosity of the porous silicon, we can make particular molecules come off it more, or less, readily. We may leave the microtips inside a cell for a predetermined time to allow molecules to disassociate themselves from the porous silicon.

Figure 1:
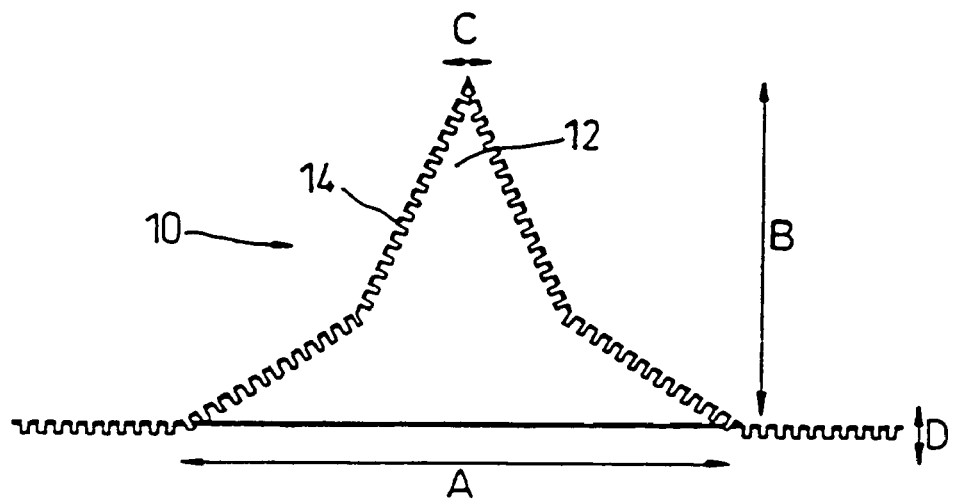
FIG. 1 shows a partially porosified silicon microtip.
Figure 2:
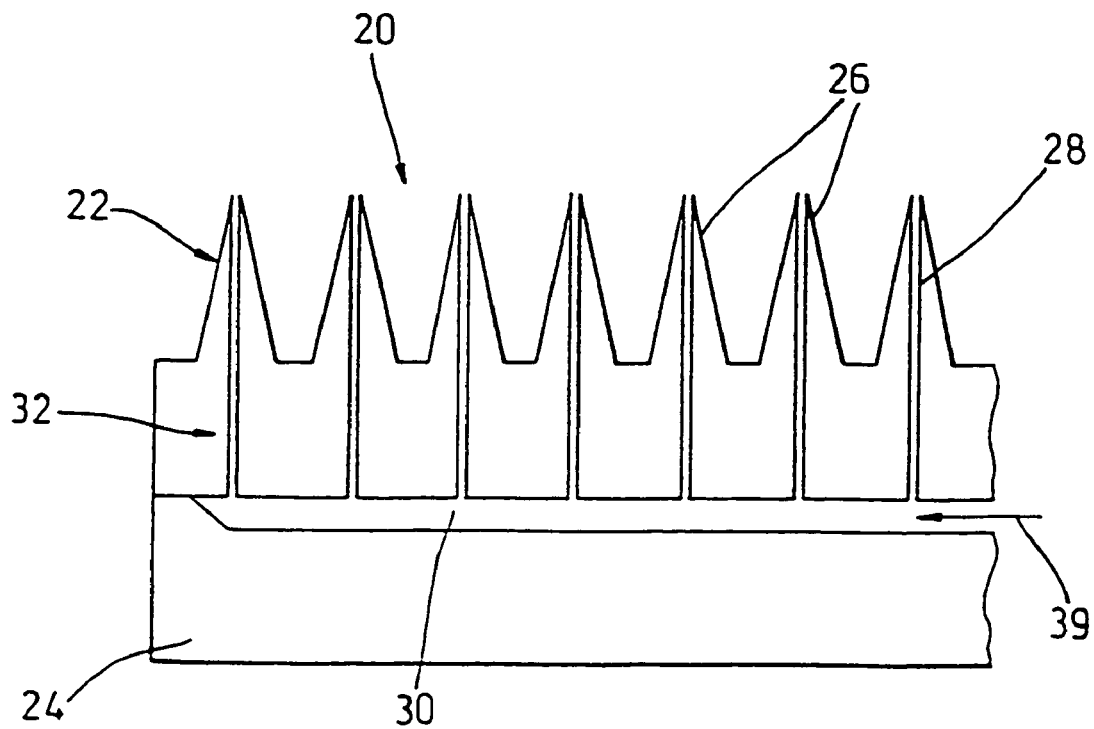
FIG. 2 shows a silicon microneedle array.

FIG. 2 shows an array 20 of silicon microneedles 22 extending away from a silicon support, or back, member 24. The microneedles 22 have porous silicon microtips 26 and a central lumen 28 communicating between the microtips 26 and a reservoir 30 defined between an upper member 32, provided with the microneedles 22 and the back, support, member 24. The back member 24 is of bulk silicon.

Figure 3:
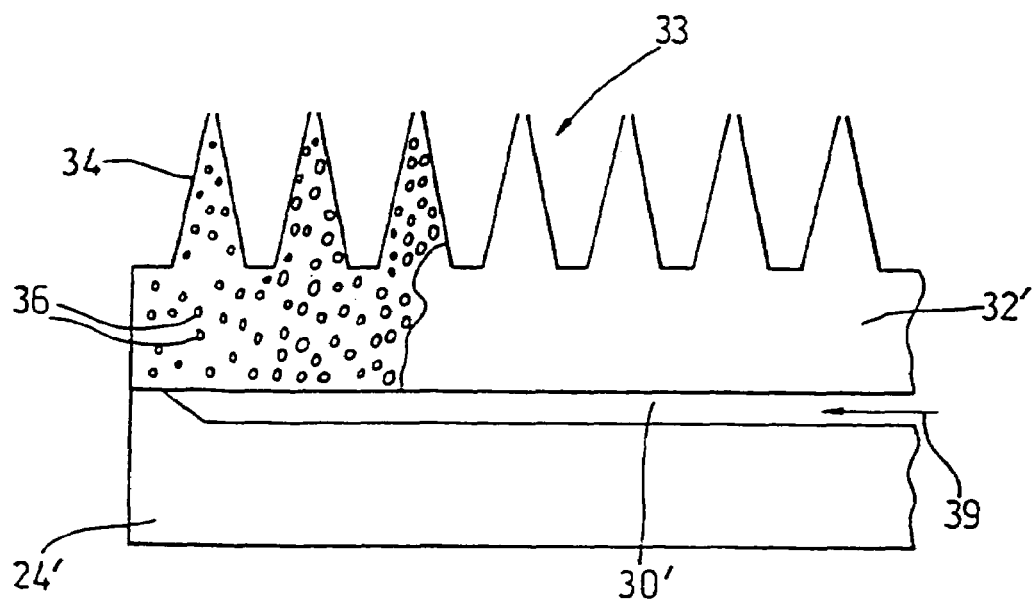
FIG. 3 shows the silicon microneedle array of FIG. 2 having a macroporous network running from the tip to an underlying reservoir.

FIG. 3 shows an array 33 of silicon microneedles 34 that is similar to that of FIG. 2. The principal difference between the arrays shown in FIGS. 2 and 3 is that the microneedles 34 shown in FIG. 3 are not provided with a central lumen 28. Instead the array 33 of silicon microneedles 34 in FIG. 3 is provided with a mesoporous network 36 which extends from the microtips of the microneedles to the reservoir 30', allowing fluid communication between the reservoir 30' and the microtips.

In use, the substance to be delivered to cells is provided to the porous silicon microtips 22,34 from the reservoir 30,30' through the central lumens 28 or the mesoporous network 36. The substance is then held by the porous silicon microtips ready for introduction into a cell.

The material to be introduced into the cells may be pumped into the reservoir 30, 30', and out through the lumens 28 or porous network by a pump, not shown (but arrow 39 indicates the pump delivering liquid to the reservoir).

All or part of the silicon surfaces within the final structure may be treated in such a way as to modify their interaction with biological systems. This might be achieved by forming a layer of porous silicon on the surface. Such a layer could be formed by either an electrochemical anodisation process or possibly by immersing the structure into a stain etching solution such as a mixture of hydrofluoric acid and nitric acid.

Figure 4:
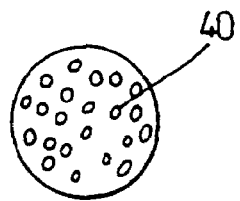
FIG. 4 shows a porous silicon bullet impregnated with DNA.

FIG. 4 shows a biolistic bullet 40 comprising a submicron silicon particle rendered mesoporous by stain etching.

In use, the bullet 40 is impregnated with the substance to be introduced into a cell and is shot into the cell using pressurised helium. As the porous silicon is a resorbable material, it will be preferably fully resorbed, and at least partially resorbed, by the cell that it entered, and thus comprises less of a foreign body than known biolistic bullets such as gold or tungsten which leave particles of metal in the cell.

Figure 5:
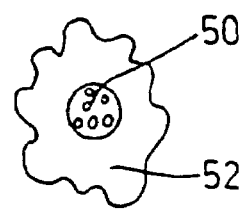
FIG. 5 shows a porous silicon core impregnated with DNA and surrounded by calcium phosphate.

FIG. 5 shows a porous silicon core 50 impregnated with a substance to be introduced into a cell (e.g. DNA/RNA) and calcium phosphate precipitate 52 formed around the core 50. The calcium phosphate 52 is co-precipitated with DNA/RNA, so that a genetic material/calcium phosphate layer surrounds the bioactive silicon core 50.

The bioactive silicon core locally induces calcium phosphate supersaturisation. It may be possible to place a bioactive silicon core next to a cell/against the wall of a cell, and co-precipitate $DNA/Ca(PO_4)_2$ against the core and against the wall of the cell. If the core is phagocytosed it can be resorbed.

The core 50 need not have DNA/RNA/any active substance on it—it may simply serve as a good nucleation site for co-precipitation of $DNA/Ca(PO_4)_2$.

It is known to use glass beads as a nucleation site for calcium phosphate co-precipitation DNA transfection—see for example the paper by Watson and Latchman in "Methods (San Diego) 1996 10(3), 289-291 (Eng).

It will be appreciated that microprobes are pores with a diameter of 2 nm or less; mesopores have a diameter of 2 nm-50 nm; and macropores have a diameter of 50 nm or more.

Figure 6:
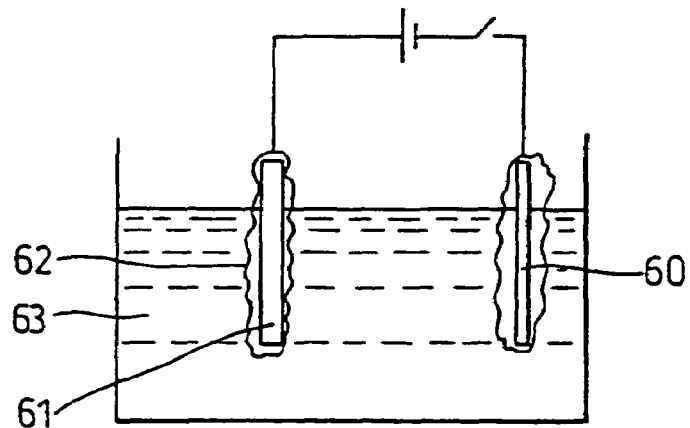
FIG. 6 illustrates the electroporation technique of the present invention.

It has also been realised that it is possible to improve the efficiency of the introduction of materials to cells in an electroporation technique, as shown in FIG. 6, using porous silicon, preferably mesoporous silicon (but macroporous and microporous silicon are also useful).

The use of a porous silicon (or porous other bioactive material, or bioactive polycrystalline silicon) electrode 60,61 achieves better performance in electroporation. Because the electrode is bioactive, instead of being bioinert cells (typically animal cells) have an affinity to it and are localised on its surface.

Low porosity (50% or less, or 30% or less, or 10% or less) bioactive silicon is electrically conducting and is a suitable intimate complex matrix for adherent mammalian cells 62, which may grow on a microelectrode array 60,61. Thus, it is possible to grow mammalian cells on bioactive porous silicon electrodes and then introduce DNA (or other substances) into the cells by using electroporation, with the substrate upon which the cells are grown being an electrode, or even both electrodes 60,61, of the electroporation apparatus. This has advantages in handling the cells, and achieves a better efficiency rate of DNA introduction than solely having the cells suspended in a liquid medium 63.

The fact that porous silicon is resorbable/erodable in vivo in mammals has been proved by the inventors, and this underpins some aspects of the invention. The fact that silicon can be made bioactive underpins other aspects of the invention.

Figure 7:
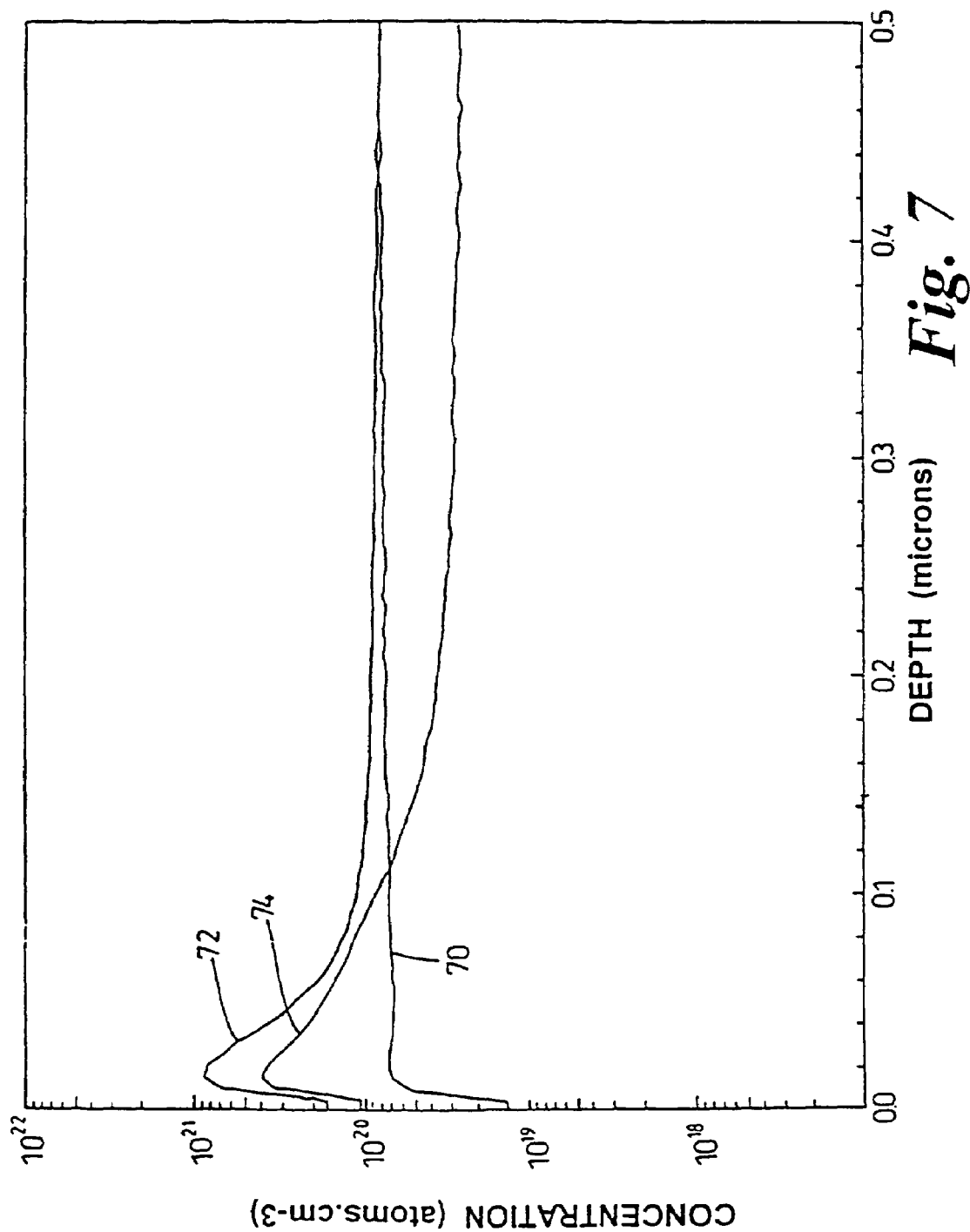

FIG. 7 shows a SIMS plot (Secondary Ion Mass Spectroscopy) showing the concentration of nitrogen with depth in a sheet of porous silicon. DNA is rich in nitrogen, and detecting high nitrogen levels in the porous silicon is a measure of how much DNA is present. Plot 70 shows the "aged" porous silicon sheet analysed for nitrogen, with no DNA added to the surface of the sheet. The background level of nitrogen depends on the type of porous silicon film and its "age"—the duration of storage in ambient air. Plot 72 shows the analysis of the porous silicon sheet after a single drop of water has been applied to the surface of the porous silicon sheet. There was 1 ng per µ litre of DNA in the drop of water. The DNA solution drop was dried at 50° C. before the sheet was analysed. Plot 74 shows the amount of nitrogen in the porous silicon when the same 1 ng per µ litre of DNA in water drop is applied to the sheet and dried, and then the sheet is washed in deionised water at 50° C.

As will be seen, there is far more nitrogen shown in plot 72 than in plot 70, showing that the DNA is being detected by the test. Plot 74 shows that the washing step removed some, but not all, of the DNA—that some of the DNA was probably partially immobilised on the porous silicon, to be released later (during washing).

FIG. 8 shows equivalent SIMS plots for the same layer after pure water treatment. "Aged" porous silicon has been stored in ambient air and has acquired a background level of nitrogen due to adsorption of nitrous oxides and ammonia—common trace pollutant gases. Plot 80 shows aged porous silicon with no DNA, plot 82 aged porous silicon with a water droplet deposit (no DNA solution), and plot 84 shows again for comparison the analysis of aged porous silicon with 1 ng/µ litre of DNA in solution added and dried at 50° C.

The SIMS data shown in FIGS. 7 and 8 demonstrate that porous silicon can reversibly bind DNA.

The invention can perhaps be thought of as using porous silicon (or perhaps polycrystalline silicon) as an inorganic vector for transporting/transferring material into a living cell.

The invention claimed is:

1. A method of transferring a substance into a cell comprising using a sub-micron silicon particle comprising silicon for conveying the substance into the cell, the particle comprising a porous surface layer.

2. A method according to claim 1 wherein the method comprises the step of transferring at least part of the silicon into the cell.

3. A method according to claim 1 wherein the porous surface layer is obtainable by a stain etch process.

* * * * *